(12) United States Patent
Von Rheinbaben et al.

(10) Patent No.: US 7,638,504 B2
(45) Date of Patent: Dec. 29, 2009

(54) HEPATITIS A VIRICIDE

(75) Inventors: Friedrich Von Rheinbaben, Monheim (DE); Holger Biering, Grevenbroich (DE); Klaus-Peter Bansemir, Langenfeld (DE); Sabine Glaeser, Dusseldorf (DE)

(73) Assignee: Ecolab Inc., St. Paul, MN (US)

( * ) Notice: Subject to any disclaimer, the term of this patent is extended or adjusted under 35 U.S.C. 154(b) by 484 days.

(21) Appl. No.: 10/168,442

(22) PCT Filed: Dec. 14, 2000

(86) PCT No.: PCT/EP00/12688

§ 371 (c)(1),
(2), (4) Date: Sep. 18, 2002

(87) PCT Pub. No.: WO01/47358

PCT Pub. Date: Jul. 5, 2001

(65) Prior Publication Data

US 2003/0060484 A1    Mar. 27, 2003

(30) Foreign Application Priority Data

Dec. 23, 1999   (DE) ................................ 199 62 353

(51) Int. Cl.
  *A61K 31/715*   (2006.01)
(52) U.S. Cl. .......................................... 514/54; 514/23
(58) Field of Classification Search ................ 514/472, 514/553, 724, 311, 23, 372, 345, 494, 54
  See application file for complete search history.

(56) References Cited

U.S. PATENT DOCUMENTS

| | | | |
|---|---|---|---|
| 4,849,455 A * | 7/1989 | Eggers et al. | 514/724 |
| 5,043,357 A | 8/1991 | Hoffler et al. | |
| 5,424,323 A | 6/1995 | Wachman et al. | |
| 5,478,829 A | 12/1995 | Conrath | 514/254 |
| 5,693,337 A | 12/1997 | Suzuki et al. | 424/450 |
| 5,728,404 A * | 3/1998 | von Rheinbaben et al. | 424/642 |
| 5,824,708 A * | 10/1998 | Disch et al. | 514/563 |
| 6,017,912 A | 1/2000 | Bussell | 514/230.02 |

FOREIGN PATENT DOCUMENTS

| | | | |
|---|---|---|---|
| AU | 650014 | * | 6/1994 |
| DE | 37 02 983 | | 12/1987 |
| DE | 36 22 089 | | 1/1988 |
| DE | 37 25 381 | | 2/1988 |
| DE | 34 30 709 | | 9/1993 |
| DE | 44 24 325 | | 8/1995 |
| DE | 197 13 850 | | 10/1998 |
| DE | 196 53 785 | | 4/1999 |
| DE | 299 00 687 U1 | | 5/1999 |
| DE | 29900687 | * | 5/1999 |
| EP | 0692192 | * | 1/1995 |
| EP | 0 692 192 | | 1/1996 |
| EP | 0692192 A1 | * | 1/1996 |
| EP | 0 848 907 | | 6/1998 |
| EP | 848907 | * | 6/1998 |
| EP | 0848907 | * | 6/1998 |
| EP | 0848907 A1 | * | 12/1998 |
| GB | 2193892 A | * | 2/1988 |
| WO | WO 99/07706 | | 2/1999 |
| WO | WO 00/18404 | | 4/2000 |

OTHER PUBLICATIONS

Mbithi, J. M. et al Comparative in vitro efficiencies of hand-washing agents against hepatitis A virus (HM-175) and Poliovirus Type 1 (Sabin), Applied and Environmental Microbiology, 1993, vol. 59, No. 10, 3463-3469.*
PGC Scientifics, 1996, p. 85.*
Wallhausser. "Praxis der Sterilisation Desinfektion-Konservierung". (Sterilization, Disinfection, and Preservation Practice), 5th Ed. Georg Thieme Verlag Stuttgart, New York, 1995, pp. 94-95, and English translation. .
"Cytotoxicity Testing of Topical Antimicrobial Agents on Human Keratinocytes and Fibroblasts for Cultured Skin Grafts", Boyce et al., Journal of Burn Care and Rehabilitation, 1995, pp. 97-103.

* cited by examiner

Primary Examiner—Shaojia Anna Jiang
Assistant Examiner—Ganapathy Krishnan
(74) Attorney, Agent, or Firm—Andrew D. Sorensen

(57) ABSTRACT

The invention relates to agents which combat the hepatitis A virus, containing only minimal amounts of chlorine-containing and/or chlorine cleaving active ingredients, or none of said substances. The inventions also relates to the use of these agents and to a method for their production.

2 Claims, No Drawings

HEPATITIS A VIRICIDE

The present invention relates to compositions which act against hepatitis A virucide and contain chlorine-containing and/or -releasing active compounds only to a very small extent or not at all.

Hand disinfectants in general have only a very restricted activity against viruses. As a rule, only the 'coated' and/or lipophilic viruses are reached. These include hepatitis B virus, HIV and rotavirus. Many further viruses, but in particular the 'uncoated' hydrophilic viruses, on the other hand, are not reached by the customary hand disinfectants. Customary hand disinfectants are frequently designed on the basis of alcohols having a total alcohol content of around 70% and are considered as inactive against the 'uncoated' hydrophilic viruses. Hepatitis A virus, probably the most important uncoated hydrophilic virus in the human medicine and the foodstuffs field, is included here. Around 5000 to 6000 hepatitis A cases are reported per year for the Federal Republic alone. These represent, however, only about 5% of the actual cases of infection. 90 to 95% of the HAV infections proceed atypically or without a marked clinical picture and are therefore not covered by the official statistics. The infection rate of HAV is thus markedly above such an important disease as, for example, HIV infection (less than 2000 new infections per year). In medical fields such as pediatrics, neonatology or infectious medicine, just as in the field of foodstuffs-processing plants, there is an urgent need for a hand disinfectant having specific activity against HAV. A fundamental activity against coated viruses (e.g. HIV, HBV) and also against bacteria and fungi is moreover an obvious fundamental requirement of such compositions, but has hitherto not been documented anywhere in combination with an HAV activity.

Hitherto, it is known that individual hand disinfectants having an ethanol concentration of 80 to 90% by volume can have an activity against poliovirus. Although poliovirus is likewise an uncoated particle, the sensitivity of the poliovirus to disinfectant recipes of this type is regarded as an exception among experts.

It is therefore required as standard for the testing of the virucidicity of hand disinfectants that they are tested against the uncoated simian virus 40. All hand disinfectants based on alcohol proved inactive here.

Despite this, there are manufacturers of hand disinfectants in the market who, on account of the activity against poliovirus, offer a virucidal action against hepatitis A as a bonus. This conclusion is not correct, since, as explained above, an inference cannot be drawn from a virus which, as is known, is sensitive to disinfectants, on another virus, no matter which. It therefore held true to this day, despite these products found on the market, for the profession that products based on alcohol have no activity against hepatitis A, since up to now a demonstration of such an activity has never been carried out.

Wallhäußer occupies himself in his book "Praxis der Sterilisation, Desinfektion, Konservierung" [Sterilization, Disinfection and Preservation Practice], 5th edition, page 94-95, Georg Thieme Verlag Stuttgart/New York, 1995, among other things, with disinfection when working with hepatitis viruses. Wallhäußer refers there to the 11th edition of the listing of experimentally tested and recognized active disinfectants and disinfection procedures required by the federal public health department of Germany according to §10c BSG and makes it clear that only chloramine T in 1 percent and 2 percent concentration meets the requirements for activity against hepatitis A. Furthermore, two commercial preparations, which are likewise based on chloro active compounds, are mentioned as preparations which are considered as active.

Accordingly, the profession, although chloro active compounds are hazardous for ecological and toxicological reasons, has thus resigned itself to the fact that it is necessary to employ chlorine-containing compositions for the control of hepatitis A. Compositions based on alcohol were considered without exception as inactive against hepatitis A viruses and were also classified as such in older editions of the BGA list. Although the need for compositions which, without aid or only with very greatly reduced amounts of chlorine-containing active compounds, have, as has been shown, an adequate activity against hepatitis A, would be very large in the market, it was not to be expected that agents of this type can be made available. It was therefore an object of the present invention to seek compositions which, with contents of chloro-active active compounds which are as low as possible, display adequate action against hepatitis A viruses.

The present invention accordingly relates to a hepatitis A-destroying composition which contains one or more aqueous alcohols and, if desired, 0.1 to 10% by weight of additional antimicrobial components, with the proviso that less than 0.5% by weight of chlorine-containing and/or chlorine-releasing active compounds are present, based on the total composition.

For the experts, it still applied that, explicitly for hepatitis A, no activity of such compositions exists. Therefore, despite the products mentioned offering HAV activity as a bonus, on account of the knowledge of the profession it was not obvious but surprising that HAV activity was to be detected for compositions according to the invention.

In a preferred embodiment of the composition according to the invention, the content of chlorine-containing and/or -releasing active compounds is less than 0.3% by weight based on the total composition, the composition according to the invention particularly preferably being free of chlorine-containing and/or -releasing active compounds.

If a chlorine-containing and/or -releasing active compound is employed in the composition according to the invention, then compounds, such as, for example, chlorhexidine gluconate, 2,2'-methylenebis(6-bromo-4-chloro-phenol), 2,4,4'-trichloro-2'-hydroxydiphenyl ether, N-(4-chlorophenyl)-N-(3,4-dichlorophenyl)urea, N,N'-bis(4-chlorophenyl)-3,12-diimino-2,4,11,13-tetraazatetradecanediimidamide are preferred.

It is preferred that the composition according to the invention contains, as alcohol, 50 to 97% by weight, particularly preferably 80 to 95% by weight, of ethanol based on the total composition, the remainder to of 100% total amount being water and/or other active compounds, optionally chlorine-containing and/or -releasing active compounds within the amounts specified.

Further additives which can be present in preferred embodiments are, by way of example, customary fragrances, refatting agents and surfactant components.

In a further preferred embodiment, the composition according to the invention contains, as a further alcohol in addition to ethanol, 0.1 to 40% by weight of one or more components selected from methanol, n-propanol, i-propanol, 1,3-butanediol, phenoxyethanol, 1,2-propylene glycol and glycerol, where the contents of the alcohols and the other components are to be chosen such that the sum of 100% is not exceeded.

Preferably, using the composition according to the invention hepatitis A is inactivated at room temperature within less than 300 seconds, particularly preferably within less than 120 seconds, and very particularly preferably within less than 60 seconds.

In a likewise preferred embodiment of the composition according to the invention, adequate effects against HAV can still be brought about even at very low temperatures of about 0° C.

As additional antimicrobial active compounds, the composition according to the invention preferably contains, based on the total composition, components which are particularly preferably selected from the groups consisting of the aldehydes, antimicrobial acids, Lewis acids, carboxylic acid esters, acid amides, phenols, phenol derivatives, diphenyls, diphenyl-alkanes, urea derivatives, oxygen and nitrogen acetals and also—formals, benzamidines, isothiazolines, phthalimide derivatives, pyridine derivatives, antimicrobial surface-active compounds, guanidines, antimicrobial amphoteric compounds, quinolines, the additional chlorine-free antimicrobial component very particularly preferably being selected from undecylenic acid, citric acid, p-hydroxybenzoic acid, sorbic acid, salicylic acid, quaternary ammonium compounds, guanidines and amphoteric compounds.

In particular, by addition of Lewis acids, for example zinc chloride, aluminum chloride and barium chloride, to the compositions according to the invention, it is possible to manage with reduced amounts of ethanol.

In a preferred embodiment, the composition according to the invention is present as a liquid, gel, cream, paste or foam, if appropriate it can also be present in the form of a combination with a solid carrier, which can be made available, for example, by impregnation or other treatment of paper, cloth fabrics or further suitable carriers.

The composition according to the invention preferably contains additional surfaceactive components such as alkyl polyglycosides.

Preferred additional excipients in the composition according to the invention are components which lead to the improvement of the skin compatibility, such as castor oil, glycerol or other alcohols, but which were already contained in the previous embodiments.

A further subject of the present invention is the use of a composition according to the invention for the disinfective treatment of skin surfaces, in particular in a microbiologically sensitive working area, very particularly in the hospital, kitchen, foodstuffs, cosmetics, pharmacy or household sector and very especially if requirements for aseptic working are made.

A further subject of the invention is a process for the production of a composition according to the invention according to the explanations made in the present invention.

EXAMPLES

For the testing of the activity against hepatitis A, 2 different recipes were selected:

Recipe A:
80% by weight of ethanol
15% by weight of methanol
remainder to 100%:
additional chlorine-free excipients, such as refatting agents, perfume etc.. and water Recipe B:
90% by weight of ethanol
0.2% by weight of chlorhexidine gluconate
remainder to 100%:
additional chlorine-free excipients, such as refatting agents, perfume etc.. and water The suspension experiments for the testing of the activity against hepatitis A were carried out according to the guidelines of the BGA (Federal public health department) and the DVV (German veterinary regulations).

The recipes A and B were incubated at room temperature with the hepatitis A virus according to the test procedure in 80% concentration without and with albumin loading.

After the specified time of action, the virus-disinfectant suspension was transferred to a microtiter plate prepared according to the experimental procedures mentioned and subsequently diluted in log 10 steps.

The dilutions were transferred to cell culture plates.

The toxicity controls were likewise carried out according to the guidelines of the BGA and of the DVV. Both in the case of recipe A and in the case of recipe B, cell damage no longer occurred at a dilution of $10^{-3}$.

The result of the inactivation experiments can be summarized as follows:

Both recipe A and recipe B inactivate the hepatitis A virus both without and with albumin loading by more than 5 titer stages (log 10) with a time of action of at least 1 minute.

After a 5-minute time of action, residual infectiousness is no longer detectable.

Thus it is confirmed for the first time that compositions according to the invention have activity against hepatitis A.

The invention claimed is:

1. A method for inactivating hepatitis A virus on skin surfaces of hands comprising:
    washing hands with an inactivating composition for a length of time sufficient to provide 4 log reduction of the hepatitis A virus, wherein:
    the inactivating composition comprising 80% to 90% by weight of ethanol, based on the total composition, alkyl polyglycoside, and water, the composition being free of chlorine-containing and/or chlorine-releasing active compounds, and the composition being provided on a solid carrier.

2. The method of claim 1, wherein the solid carrier comprises paper or cloth fabric.

* * * * *

UNITED STATES PATENT AND TRADEMARK OFFICE
CERTIFICATE OF CORRECTION

PATENT NO. : 7,638,504 B2
APPLICATION NO. : 10/168442
DATED : December 29, 2009
INVENTOR(S) : Von Rheinbaben et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 572 days.

Signed and Sealed this

Ninth Day of November, 2010

David J. Kappos
*Director of the United States Patent and Trademark Office*